United States Patent [19]

Wons

[11] Patent Number: 4,490,835
[45] Date of Patent: Dec. 25, 1984

[54] X-RAY EXAMINATION DEVICE EMPLOYING DOUBLE-SLIT BEAM COLLIMATION

[75] Inventor: Heinz Wons, Erlangen, Fed. Rep. of Germany

[73] Assignee: Siemens Aktiengesellschaft, Berlin & Munich, Fed. Rep. of Germany

[21] Appl. No.: 421,398

[22] Filed: Sep. 22, 1982

[30] Foreign Application Priority Data

Sep. 30, 1981 [DE] Fed. Rep. of Germany ....... 3138939

[51] Int. Cl.³ ............................................. G03B 41/16
[52] U.S. Cl. ..................................... 378/146; 378/147
[58] Field of Search ....................... 378/146, 99, 7, 19, 378/4, 147

[56] References Cited

U.S. PATENT DOCUMENTS 4,097,748 6/1978 Monvoisin ........................... 250/505
4,203,037 5/1980 Gur et al. ............................ 250/505

FOREIGN PATENT DOCUMENTS 716880 1/1942 Fed. Rep. of Germany .
2732073 1/1978 Fed. Rep. of Germany .
2814242 10/1979 Fed. Rep. of Germany .

OTHER PUBLICATIONS

"Slit Radiography Method Comprising a Co-Guided Radiator," R. Moore and K. Amplatz, Electromedica, vol. 49, No. 1, pp. 34–41, Jan. 1981 (plus translation).

Moore et al., "A Method to Absorb Scattered Radiation Without Attenuation," *Radiology*, vol. 120, 1976, pp. 713–717.

*Primary Examiner*—Alfred E. Smith
*Assistant Examiner*—T. N. Grigsby
*Attorney, Agent, or Firm*—Hill, Van Santen, Steadman & Simpson

[57] ABSTRACT

An X-ray examination device has an X-ray tube, a primary X-ray diaphragm attached to the X-ray tube and disposed close to the focus thereof, a patient support bed, and an X-ray exposure device disposed behind the patient's support bed in the radiation direction having an X-ray image carrier and a stray radiation screen. The primary X-ray diaphragm includes a first slit beam collimator for generating a fan-shaped radiation beam and the X-ray exposure device has a second slit beam collimator in the form of two displaceable diaphragm plates and an adjustment device for moving the plates relative to one another to achieve a slit opening therebetween of desired width. The examination device further includes synchronized drive units for moving the X-ray tube and the second beam collimator in fixed alignment for sweeping the radiation beam across a patient on the support bed.

11 Claims, 7 Drawing Figures

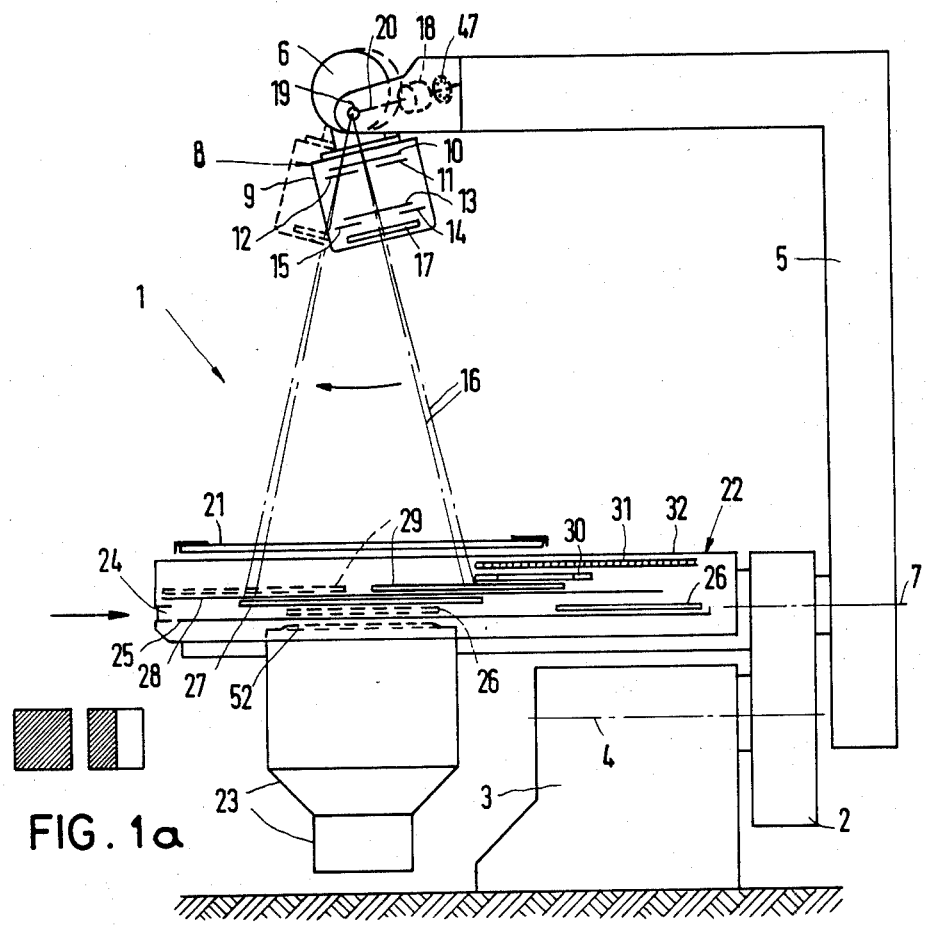
FIG. 1a
FIG 1
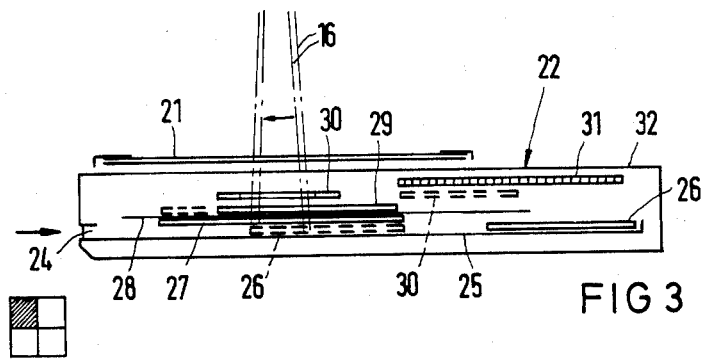
FIG. 3a
FIG 3

X-RAY EXAMINATION DEVICE EMPLOYING DOUBLE-SLIT BEAM COLLIMATION

BACKGROUND OF THE INVENTION

1. Field of the Invention

The present invention relates to X-ray examination devices, and in particular to such devices having at least two beam collimators in the form of slit diaphragms, one of which is disposed close to the focus of the X-ray tube and the other of which is disposed close to the X-ray film on which the radiation is incident.

2. Description of the Prior Art

The level of contrast and resolution of X-ray photographs, both of which contribute to the recognition of details in such photographs, are known to be increased by reducing the stray radiation component of the X-ray beam. For this purpose, a stray radiation screen disposed directly in front of the image plane of the radiation detector in the radiation direction is generally utilized for reducing the stray radiation component. Another commonly utilized method for reducing the stray radiation component is to collimate the radiation cone by utilizing only a solid angle portion thereof defined by a slit diaphragm. This segment of the X-ray beam is swept over the examination subject, and the X-ray film cassette disposed below the patient, and instead of utilizing a stray radiation screen, a second slit diaphragm which also collimates the fan-shaped radiation beam is synchronously moved in alignment with the first slit diaphragm across the X-ray film cassette. By means of this so-called "double-slit diaphragm method" not only is less stray radiation generated per time unit in the volume of the examination subject (this being a direct consequence of the reduction of the irradiated volume) but also a negligibly small portion of the stray radiation which is present strikes the X-ray film due to the presence of the second slit diaphragm. In exchange for these advantages, however, the equipment outlay for the synchronous control of the two slit diaphragms is increased and longer exposure times with a corresponding higher X-ray tube load are required.

A known X-ray examination device for generating X-ray photographs according to the double slit diaphragm method is described in U.S. Pat. No. 4,097,748. In this X-ray examination device, the fan-shaped radiation beam segment of the X-ray beam cone is conducted across the examination area perpendicularly with respect to the plane of the fan. The second beam collimator, that is, the second slit diaphragm, is disposed in the radiation direction directly in front of the X-ray film plane and is moved across the film plane synchronously with the fan shaped radiation beam in alignment therewith. To this end, the motor which adjusts the position of the X-ray tube (and the first slit diaphragm attached thereto) and the other motor which displaces the second slit diaphragm disposed above the film plane are controlled in such a manner that the fan-shaped radiation beam is always in registry with those two slit diaphragms. A characteristic of this design is that the outlay for the synchronous movement of the two slit diaphragms considerably increases as the diaphragm slit width becomes smaller because of the increased demands made on the precision of the control means. Recognition of detail on the X-ray photograph, however, improves as the slit diaphragm (and the fan-shaped radiation beam) is made narrower. This known device has the further disadvantage that a user of this type of X-ray device who wishes to retain the capability of conducting an X-ray examination using the entire radiation cone with a stray radiation screen, instead of the double slit method, must either purchase two X-ray devices or make a choice between the full beam method and the double slit method.

SUMMARY OF THE INVENTION

It is an object of the present invention to provide an X-ray examination apparatus which can be selectively operated in a full beam mode utilizing a stray beam screen or in a collimated beam mode utilizing two slit diaphragms.

It is a further object of the present invention to provide an X-ray examination apparatus operable in a double slit beam collimating mode wherein the width of at least one of the slits can be selectively varied.

The above objects are inventively achieved in an X-ray examination device having an X-ray tube and a primary X-ray diaphragm attached to the X-ray tube and disposed close to the focus thereof for directing radiation toward and through a patient so as to be incident on an image layer of an X-ray detector, wherein the primary X-ray diaphragm has a first beam collimator in the form of a slit diaphragm and the X-ray detector also has a slit diaphragm functioning as a second beam collimator, the slit diaphragm of the X-ray detector being formed by two displaceable diaphragm plates which are movable relative to one another so that the spacing between the plates forming the slit diaphragm can be selectively varied. A synchronous drive means is provided for moving the X-ray tube (and the first beam collimator attached thereto) in alignment with the second beam collimator in a sweep of the radiation beam across a patient. If the X-ray apparatus is desired to be utilized in a full beam mode, that is, with no double slit collimating of the X-ray beam, the diaphragm plates forming the second beam collimating means can be moved far enough apart so as to be out of the path of the radiation beam and a stray radiation screen is moved into the position formerly occupied by the diaphragm plates in the beam path. Thus, a single X-ray examination unit can be operated in a double slit beam collimating mode or a full beam mode as desired.

In a further embodiment of the invention, at least one of the diaphragm plates may carry one or more detents against which the other diaphragm plate abuts as the plates are moved toward each other so as to fix a minimum width of the second slot diaphragm formed therebetween. By so doing, a precise adjustment of the slit diaphragm is achieved in a simple manner.

The adjustment of the displaceable diaphragm plates can be further facilitated and simplified in another embodiment of the invention wherein at least one spring is connected to each of the diaphragm plates normally urging the plates toward one another. The plates will thus automatically move toward one another when decoupled from the normally-engaged drive means.

In another embodiment of the invention, the movement of the diaphragm plates toward and away from each other is achieved by a separate drive unit which is synchronized with the drive units for moving the X-ray tube and the second slit diaphragm formed by the plates.

As stated above, the combination of the diaphragm plates forming the second diaphragm can be moved in common by a separate drive means in a direction perpendicular to the edges of the plates which limit the radiation beam such that the spacing between the plates is unchanged as the plates are moved. This feature also permits subdivided conventional exposures to be made.

A releaseable coupling may be included in the drive train for controlling the spacing between the two plates which facilitates switching from a conventional or full beam exposure mode to the double slit diaphragm mode by simply actuating the drive means with the coupling engaged.

BRIEF DESCRIPTION OF THE DRAWINGS

FIG. 1 is a side view of an X-ray examination device constructed in accordance with the principles of the present invention.

FIG. 1a is a plan view of the radiation pattern obtained in the device shown in FIG. 1.

FIG. 3 is a schematic illustration of the position of the diaphragm plates in the X-ray table shown in FIG. 2 for achieving a subdivided X-ray exposure.

FIG. 3a is a schematic representation of the beam pattern for the embodiment shown in FIG. 3.

DESCRIPTION OF THE PREFERRED EMBODIMENTS

Figure 2:
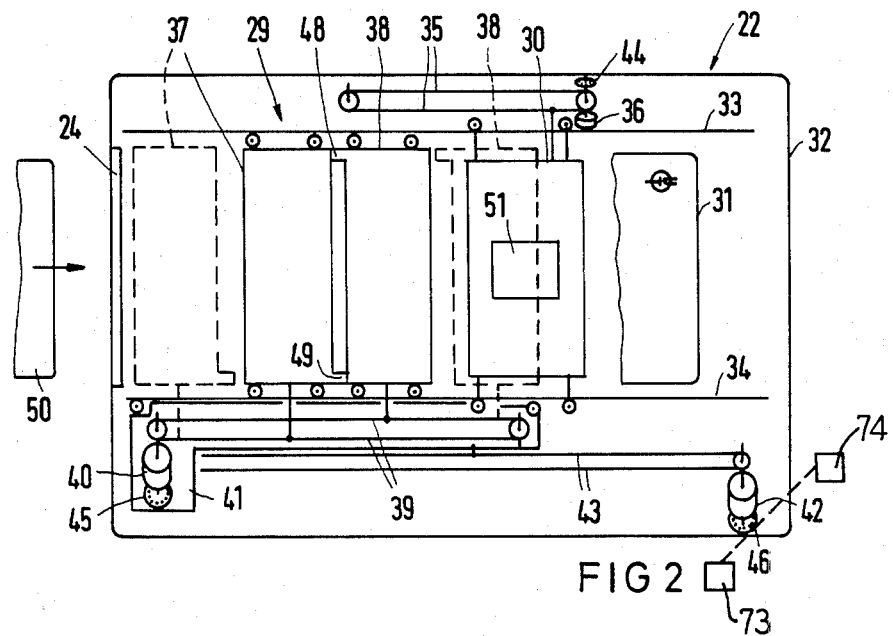
FIG. 2 is a plan view of a first embodiment of the X-ray table shown in FIG. 1.

An X-ray examination device 1 is shown schematically in side view in FIG. 1. The examination device 1 has a table frame 2 seated on a pedestal 3 pivotable about a horizontal tilt axis 4. A support column 5 for an X-ray tube 6 is mounted on the table frame 2 and is pivotable around a further horizontal axis 7 which is parallel to the tilt axis 4. A primary X-ray diaphragm 8 is connected to the X-ray tube 6, such as by flanges.

The primary ray diaphragm 8 has a housing 9 containing diaphragm plates 10, 11, 12, 13 and 15 by means of which the radiation beam 16 is collimated. The primary X-ray diaphragm 8 also includes a further slit diaphragm 17 disposed close to the focus 19 of the X-ray tube 6 which can be moved in and out of the radiation field. The slit diaphragm 17 forms a first collimator in a double slit diaphragm system.

A positioning motor 18 is connected to the X-ray tube 6 by means of which the X-ray tube 6, together with the primary X-ray diaphragm 8, can be pivoted about an axis 20 proceeding through the focus 19.

A patient support bed 21 is displaceably mounted on the table frame 2 by any suitable manner known to those skilled in the art, the details of which are not illustrated further in FIG. 1. An X-ray table or target device 22 is mounted on the table frame 2. Below, the table 22 is an image intensifier, television camera 23. A cassette insert opening 24 and a transport track 25 for an X-ray film cassette 26 are disposed at the left side of the table 22 as shown in FIG. 1. The cassette 26 is shown in FIG. 1 to be in a ready position. An ionization chamber 27 is disposed above the transport track 25 in an exposure position, that is, in the field of the radiation beam 16. A slit diaphragm 29 is disposed above the ionization chamber 27 mounted on a further transport track 28 so as to be displaceable in a plane parallel to the plane of the cassette 26. A frame diaphragm plate 30 is also mounted in the table 22 above the slit diaphragm 29 in the direction of radiation. The frame diaphragm 30 can be displaced from the ready position shown in FIG. 1 to an exposure position in the radiation path. A stray radiation screen 31 is also contained in the table 22 which is shown in FIG. 1 in a ready position disposed above the frame diaphragm plate 30 in the radiation direction.

A plan view of the X-ray table 22 showing the positioning means for the various diaphragm plates is shown in FIG. 2. All elements described below are contained in a target device housing 32. The frame-diaphragm plate 30, having a central opening 51, is displaceable along two parallel rails 33 and 34 from a ready position to an exposure position and back. For this purpose, the frame diaphragm plate 30 is connected to a continuous toothed belt 35 which is driven by a motor 36.

The slit diaphragm 29 is also displaceable along the parallel rails 33 and 34. As can be seen in FIG. 2, the slit diaphragm 29 is formed by two diaphragm plates 37 and 38 mounted above the film cassette 26 which are separately connected to another continuous toothed belt 39 which is driven by a motor 40. The diaphragm plates 37 and 38, the toothed belt 39 and the drive motor 40 are all mounted on a carriage 41. The carriage 41 is displaceable along the lower rail 34 in the housing 32. For this purpose, the carriage 41 is connected to another continuous toothed belt 43 driven by a motor 42.

All three of the motors 36, 40 and 42, as well as the positioning motor 18 for pivoting the X-ray tube 6, have respective perforated discs 44, 45, 46 and 47 mounted on their drive shafts, the apertures at the periphery of the perforated discs being rotated between a light source and a photodetector. for synchronizing the motors in a known manner. A light source 73 and a photodetector 74 associated with the perforated disc 46 are schematically shown in FIG. 2, however, it will be understood that each of the other perforated discs has identical components associated therewith which are omitted for clarity. The drive system may be set to permanently fix the synchronization and alignment of the slit diaphragms.

The edges of the plates 37 and 38 facing each other have respective detents 48 and 49 carried thereon so as to maintain a minimum spacing between the plates as the plates are moved toward each other so as to fix a minimum width for the slit diaphragm 29. The minimum spacing dictated by the detents 48 and 49 is equal to the width of the slit in the first slit diaphragm 17. FIG. 2 also shows an X-ray film cassette 50 to be inserted in the housing 32 in the direction of the arrow via the cassette insert opening 24. The stray radiation screen 31 is shown in FIG. 2 in the ready position.

An X-ray target device 22 of the type shown in FIG. 1 and FIG. 2 is shown in FIG. 3 with the diaphragms therein positioned for achieving a multiple subdivision of the film in the X-ray film cassette 26. The multiple subdivision is schematically shown in FIG. 3a. For this purpose, the frame diaphragm plate 30 is introduced into the exposure position in the radiation beam path in addition to the diaphragm plates 37 and 38 comprising the second slit diaphragm 29. The frame diaphragm plate 30 prevents certain areas of the X-ray film cassette 26 which are disposed outside of the opening 51 of the frame diaphragm plate 30 from being exposed. For four-fold subdivision of the film, the sub-field of the film or of the X-ray cassette 26 must be centered relative to the center of the opening 51 of the frame diaphragm plate 30. This requires displacement of the X-ray film cassette 26 perpendicularly with respect to the plane of the drawing. In this mode of operation, radiation is emitted by the X-ray tube 6 only after the X-ray tube 6 and the primary X-ray diaphragm 8 connected thereto and the second slit diaphragm 29 formed by the diaphragm plates 37 and 38 have been approximately aligned so that the fan-shaped radiation 16 begins to sweep the opening 51 of the frame diaphragm plate 30. The radiation is switched off as soon as the fan-shaped ray 16 reaches the opposite side of the opening 51 in the frame diaphragm plate 30.

Figure 4:
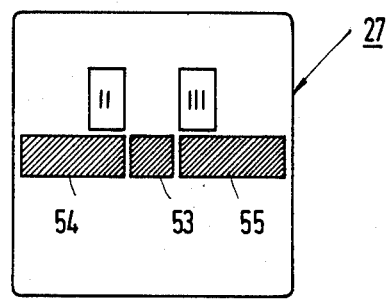
FIG. 4 is a plan view of the measuring chambers used in the ionization chamber in the device shown in FIG. 1.

A plan view of the ionization chamber 27 by means of which the X-ray tube current is controlled is shown in FIG. 4. This ionization chamber is similar to a conventional three-field ionization chamber, however, two additional narrow measuring fields 54 and 55 have been added at both sides of the central measuring field 53. During operation of the X-ray examination device 1 in the double slit diaphragm mode, the two additional measuring fields 54 and 55 and the central measuring field 53 are all switched on. As a consequence of the uniform width of the fields, the dose rate can thus be controlled according to the thickness of the radiation subject during the entire sequence of motion of the first and second beam collimating means formed by the primary X-ray diaphragm 8 and the slit diaphragm 29.

If a conventional or full beam X-ray photograph is to be produced with the examination device 1 shown in FIGS. 1 through 3, the X-ray film cassette 26 is inserted through the cassette insert opening 24 and is transported by any suitable means known to those skilled in the art not shown in greater detail in the figures along the transport track 25 into a ready position beneath the stray radiation screen shown in FIG. 1, which is also in a ready position. The width of the exposure field can be set in a known manner by suitable adjustment of the diaphragm plates 10, 11, 12, 13, 14 and 15 of the primary X-ray diaphragm 8. For this purpose, the first slit diaphragm is withdrawn from the radiation field and the two diaphragm plates 37 and 38 comprising the slit diaphragm 29 are moved apart by the motor 40 to the positions indicated by the dashed lines in FIG. 2. The stray radiation screen 31 and the film cassette 26 are moved to an exposure position in the path of the radiation for exposure of the film. As needed, an additional subdivision or limitation of the format can be achieved by additionally introducing the frame diaphragm plate 30 in the radiation path.

For operation of the examination device 1 shown in FIG. 1 in the double slit diaphragm or collimated beam mode, the stray radiation screen 31 remains in the ready position shown in FIG. 1. The slit diaphragm 17 is inserted in the radiation field of the primary X-ray diaphragm 8 and the diaphragm plates 37 and 38 comprising the second slit diaphragm 29 are transported by the motor 40 to the minimum spacing position prescribed by the detents 48 and 49. The carriage 41 together with the motor 40 and the diaphragm plates 37 and 38 are brought to an extreme position by the motor 42. The primary X-ray diaphragm 8 is also rotated to an extreme position together with the X-ray tube 6 by the positioning motor 18, at which extreme position the fan-shaped radiation beam passes through the first slit diaphragm 17 and the second slit diaphragm 29 formed by the two diaphragm plates 37 and 38. Proceeding from this starting position, the carriage 41 (and the diaphragm 29) are moved over the X-ray film cassette 26 situated in the exposure position and, synchronously therewith, the primary X-ray diaphragm is pivoted in combination with the X-ray tube 6 such that the fan-shaped radiation beam 16 is always aligned relative to the aperture in the first slit diaphragm 17 and the aperture in the second slit diaphragm 29 formed by the diaphragm plates 37 and 38. The synchronization of the motors 18 and 40 is achieved, as described above, by the perforated discs mounted on the shafts of the motors rotating between respective light sources and photodetectors. The pulses counted in the photodetectors, such as photodetector 74, are utilized for synchronizing the motors in a manner not illustrated in further detail. The output of the X-ray tube 6 is controlled by means of the ionization chamber 27 with the two narrow measuring fields 54 and 55 being swept by the fan-shaped radiation beam 16 as well as the central measuring field 53. All three measuring fields are switched on.

After the entire sheet of film in the X-ray film cassette 26 is to be exposed, the X-ray film cassette 26 is centrally positioned over an input luminescent screen 52 of the X-ray image intensifier 23, as shown in dashed lines in FIG. 1. If, however, a two-fold subdivision of the film is to be undertaken, the X-ray film cassette 26, as shown in dashed lines in FIG. 3, is only introduced into the exposure position to such an extent that the sub-field to be exposed is positioned centrally relative to the exposure area, that is, centrally relative to the mean perpendicular of the X-ray image intensifier 23, which is always centered relative to the exposure area. In this case, the X-ray tube 6 emits radiation only in that portion of the total swivel range during which the fan-shaped X-ray beam 26 sweeps the field of the X-ray film cassette to be exposed, that is, the displacement of the first slit diaphragm 17 and the second slit diaphragm 29 is only undertaken in this range.

Figure 5:
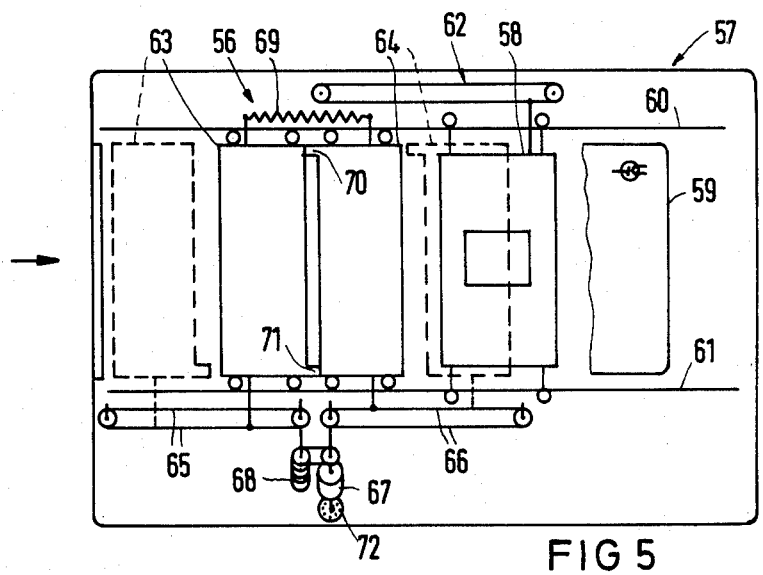
FIG. 5 is a plan view of a second embodiment of an X-ray table constructed in accordance with the principles of the present invention which may be utilized in the device shown in FIG. 1.

Another embodiment for the drive means associated with the second slit diaphragm is shown in FIG. 5, this embodiment being contained in a target device or table 57 shown in FIG. 5. The second slit diaphragm 56 is in this embodiment also formed by diaphragm plates 63 and 64 and the target device 57 also includes a frame diaphragm plate 58, a stray radiation screen 59, rails 60 and 61, and a drive unit 62 for the frame diaphragm plate 58, all of which are identical to the corresponding elements described in connection with FIG. 2. In this embodiment, however, the carriage 41 and the motor 42 and toothed belt 43 associated therewith in the embodiment shown in FIG. 2 have been eliminated. Instead, two separate continuous toothed belts 65 and 66 which are synchronously driven in the same direction by a common motor 67 are utilized for opposed adjustment of the two diaphragm plates 63 and 64 forming the second slit diaphragm 56. A disengageable coupling 68 is included in the transmission path of one of the diaphragm plates, such as the diaphragm plate 63. The two diaphragm plates 63 and 64 are urged toward one another by a tension spring 69 connected therebetween.

If the coupling 68 is engaged, the two diaphragm plates 63 and 64 can be adjusted in opposition by the motor 67. As a result, the width of the exposure field can be varied as desired given conventional X-ray exposures. When transferring to the double slit beam mode, the coupling 68 need merely be disengaged after the motor-driven approach of the diaphragm plates 63 and 64. The diaphragm plates 63 and 64 will be maintained seated against the detents 70 and 71 by the tension spring 69. The two diaphragm plates 63 and 64 can thus be displaced in common at right angles relative to the slit direction by the motor 67 when the coupling 68 is engaged. This has the advantage that only a single motor is needed to either vary the width of the exposure field when using a full radiation beam and to move the diaphragm plates against each other across the exposure field in the double slit diaphragm mode.

It will be apparent to those skilled in the art that the primary X-ray diaphragm 8 connected to the X-ray tube 6 may be utilized to collimate the beam by means of the diaphragm plates 10, 11, 12, 13, 14 and 15, in which case the separate slit diaphragm 17 may be eliminated. Other modifications may be employed without departing from the inventive concept disclosed and claimed herein, such as substituting chain drives in place of the toothed belts.

Although other modifications and changes may be suggested by those skilled in the art it is the intention of the inventor to embody within the patent warranted hereon all changes and modifications as reasonably and properly come within the scope of his contribution to the art.

I claim as my invention:

1. An X-ray examination device comprising:
   an X-ray tube;
   a primary X-ray diaphragm disposed in front of and close to the focus of said X-ray tube,
      said primary X-ray diaphragm including means defining a first slit diaphragm for collimating radiation from said X-ray tube;
   a patient support bed;
   an X-ray exposure table disposed behind said patient support bed in the radiation direction, said exposure table having an X-ray image carrier, a displaceable stray radiation screen movable in front of said image carrier in and out of the radiation field, and a second slit diaphragm disposed above said image carrier formed by two displaceable diaphragm plates and a means for adjusting the spacing between said diaphragm plates to a minimum diaphragm plate spacing which corresponds to the width of the slit in said first slit diaphragm;
   a drive means connected to said X-ray tube and to said second slit diaphragm for synchronously moving said X-ray tube, said first slit diaphragm, and said second slit diaphragm in fixed alignment in a sweep across said patient support bed in a direction perpendicular to the slits in said first and second slit diaphragms; and
   said primary X-ray diaphragm being attached to said X-ray tube for comovement therewith, and said drive means including a positioning motor connected to said X-ray tube for pivoting said X-ray tube and said primary X-ray diaphragm perpendicularly relative to the plane of the radiation beam formed by said first slit diaphragm in said primary X-ray diaphragm about an axis which proceeds through said focus of said X-ray tube.

2. An X-ray examination device comprising:
   an X-ray tube;
   a primary X-ray diaphragm disposed in front of and close to the focus of said X-ray tube,
      said primary X-ray diaphragm including means defining a first slit diaphragm for collimating radiation from said X-ray tube;
   a patient support bed;
   an X-ray exposure table disposed behind said patient support bed in the radiation direction, said exposure table having an X-ray image carrier, a displaceable stray radiation screen movable in front of said image carrier in and out of the radiation field, and a second slit diaphragm disposed above said image carrier formed by two displaceable diaphragm plates and a means for adjusting the spacing between said diaphragm plates to a minimum diaphragm plate spacing which corresponds to the width of the slit in said first slit diaphragm;
   at least one detent carried on at least one of said diaphragm plates for stopping adjustment of said diaphragm plates toward each other at a selected spacing which is said minimum spacing; and
   a drive means connected to said X-ray tube and to said second slit diaphragm for synchronously moving said X-ray tube, said first slit diaphragm, and said second slit diaphragm in fixed alignment in a sweep across said patient support bed in a direction perpendicular to the slits in said first and second slit diaphragms.

3. The X-ray examination device of claim 2 further comprising at least one spring connected between said diaphragm plates normally urging said diaphragm plates toward each other.

4. The X-ray examination device of claim 3 further comprising a disengageable coupling interconnected between said drive means and one of said diaphragm plates.

5. The X-ray examination device of claim 2 wherein said drive means includes a drive motor for displacing said diaphragm plates in common in a direction perpendicular to the edges of said plate forming said second slit diaphragm while maintaining the spacing between said plates unaltered.

6. The X-ray examination device of claim 2 wherein said drive means permanently fixes said alignment of said first and second slit diaphragms.

7. The X-ray examination device of claim 2 wherein said drive means includes at least two motors respectively connected to said second slit diaphragm and to said X-ray tube and wherein each of said motors has a drive shaft with a perforated disc mounted thereon, said disc rotating between a light source and a photodetector for generating a series of pulses for synchronizing movement of said X-ray tube and said second slit diaphragm in alignment.

8. An X-ray examination device comprising:
   an X-ray tube;
   a primary X-ray diaphragm disposed in front of and close to the focus of said X-ray tube,
      said primary X-ray diaphragm including means defining a first slit diaphragm for collimating radiation from said X-ray tube;
   a patient support bed;
   an X-ray exposure table disposed behind said patient support bed in the radiation direction, said exposure table having an X-ray image carrier, a displaceable stray radiation screen movable in front of said image carrier in and out of the radiation field, and a second slit diaphragm disposed above said image carrier formed by two displaceable diaphragm plates and a means for adjusting the spacing between said diaphragm plates to a minimum diaphragm plate spacing which corresponds to the width of the slit in said first slit diaphragm;

a drive means connected to said X-ray tube and to said second slit diaphragm for synchronously moving said X-ray tube, said first slit diaphragm, and said second slit diaphragm in fixed alignment in a sweep across said patient support bed in a direction perpendicular to the slits in said first and second slit diaphragms; and a further drive means connected to said diaphragm plates for moving said diaphragm plates toward or away from each other.

9. An X-ray examination device comprising:

an X-ray tube;

a primary X-ray diaphragm disposed in front of and close to the focus of said X-ray tube,
  said primary X-ray diaphragm including means defining a fist slit diaphragm for collimating radiation from said X-ray tube;

a patient support bed;

an X-ray exposure table disposed behind said patient support bed in the radiation direction, said exposure table having an X-ray image carrier, a displaceable stray radiation screen movable in front of said image carrier in and out of the radiation field, and a second slit diaphragm disposed above said image carrier formed by two displaceable diaphragm plates and a means for adjusting the spacing between said diaphragm plates to a minimum diaphragm plate spacing which corresponds to the width of the slit in said first slit diaphragm;

a drive means connected to said X-ray tube and to said second slit diaphragm for synchronously moving said X-ray tube, said first slit diaphragm, and said second slit diaphragm in fixed alignment in a sweep across said patient support bed in a direction perpendicular to the slits in said first and second slit diaphragms; and a displaceable fram diaphragm plate movable in front of said diaphragm plates in and out of said radiation field perpendicularly to the slit in said second slit diaphragm for limiting the radiation field incident on said image carrier.

10. An X-ray examination device comprising:

an X-ray tube;

a primary X-ray diaphragm disposed in front of and close to the focus of said X-ray tube,
  said primary X-ray diaphragm including a displaceable slotted diaphragm plate defining a first slit diaphragm for collimating radiation from said X-ray tube, said slotted diaphragm plate being movable in and out of said radiation field;

a patient support bed;

an X-ray exposure table disposed behind said patient support bed in the radiation direction, said exposure table having an X-ray image carrier, a displaceable stray radiation screen movable in front of said image carrier in and out of the radiation field, and a second slit diaphragm disposed above said image carrier formed by two displaceable diaphragm plates and a means for adjusting the spacing between said diaphragm plates to a minimum diaphragm plate spacing which corresponds to the width of the slit in said first slit diaphragm;

a drive means connected to said X-ray tube and to said second slit diaphragm for synchronously moving said X-ray tube, said first slit diaphragm, and said second slit diaphragm in fixed alignment in a sweep across said patient support bed in a direction perpendicular to the slits in said first and second slit diaphragms.

11. An X-ray examination device comprising:

an X-ray tube;

a primary X-ray diaphragm disposed in front of and close to the focus of said X-ray tube,
  said primary X-ray diaphragm including means defining a first slit diaphragm for collimating radiation from said X-ray tube;

a patient support bed;

an X-ray exposure table disposed behind said patient support bed in the radiation direction, said exposure table having an X-ray image carrier, a displaceable stray radiation screen movable in front of said image carrier in and out of the radiation field, and a second slit diaphragm disposed above said image carrier formed by two displaceable diaphragm plates and a means for adjusting the spacing between said diaphragm plates to a minimum diaphragm plate spacing which corresponds to the width of the slit in said first slit diaphragm;

a drive means connected to said X-ray tube and to said second slit diaphragm for synchronously moving said X-ray tube, said first slit diaphragm, and said second slit diaphragm in fixed alignment in a sweep across said patient support bed in a direction perpendicular to the slits in said first and second slit diaphragms; and an ionization chamber in said X-ray exposure table, said ionization chamber having two spaced narrow connectable measuring chambers disposed perpendicular to the slit in said second slit diaphragm for measuring the intensity of said radiation from said X-ray tube and for controlling the dose rate of said X-ray tube.

* * * * *